(12) United States Patent
Hsu

(10) Patent No.: US 8,579,900 B2
(45) Date of Patent: Nov. 12, 2013

(54) MINIMALLY INVASIVE SKELETAL FIXATION DEVICE

(76) Inventor: Chia-Hao Hsu, Kaohsiung (TW)

( * ) Notice: Subject to any disclaimer, the term of this patent is extended or adjusted under 35 U.S.C. 154(b) by 270 days.

(21) Appl. No.: 12/654,851

(22) Filed: Jan. 6, 2010

(65) Prior Publication Data

US 2011/0166574 A1    Jul. 7, 2011

(51) Int. Cl.
- *A61B 17/56* (2006.01)
- *A61B 17/58* (2006.01)
- *A61B 17/82* (2006.01)
- *A61F 2/30* (2006.01)

(52) U.S. Cl.
USPC .............................. 606/74; 606/139

(58) Field of Classification Search
USPC ....... 606/54, 60, 74, 86 R, 88, 151, 320, 324, 606/57, 89, 96–98, 103–105
See application file for complete search history.

(56) References Cited

U.S. PATENT DOCUMENTS

| | | | | |
|---|---|---|---|---|
| 5,071,428 A | * | 12/1991 | Chin et al. | 606/184 |
| 6,086,596 A | * | 7/2000 | Durham | 606/103 |
| 2004/0204717 A1 | * | 10/2004 | Fanger et al. | 606/96 |
| 2005/0234469 A1 | * | 10/2005 | Whittaker et al. | 606/98 |
| 2006/0030839 A1 | * | 2/2006 | Park et al. | 606/1 |
| 2008/0208205 A1 | * | 8/2008 | Kraemer | 606/103 |

* cited by examiner

*Primary Examiner* — Andrew Yang
*Assistant Examiner* — Diana S Jones
(74) *Attorney, Agent, or Firm* — Meagher Emanuel Laks Goldberg & Liao, LLP

(57) ABSTRACT

A minimally invasive skeletal fixation device includes two curved tubes and two positioning members. The two curved tubes are attached to each other and are in communication with each other. The positioning members are coupled to the curved tubes. The device is applicable to surgical operations for treating bone fractures and offers the advantages of small incision size, simple structure, easy operation, improved performance of surgical operation, and flexible adjustment of installation sites of Kirschner pins.

1 Claim, 21 Drawing Sheets

MINIMALLY INVASIVE SKELETAL FIXATION DEVICE

FIELD OF THE INVENTION

The present invention relates to a minimally invasive skeletal fixation device, and in particular to a minimally invasive skeletal fixation device having a special assembly comprising two curved tubes and two positioning members, which offers advantages of small incision size, simple structure, and easy operation and is applicable to surgical operations for treating bone fractures.

BACKGROUND OF THE INVENTION

When human bodies or animals are hurt in sport injuries or in accidents, bones are often fractured due to being hit by strong external force. Treatment of bone fracture is often carried out through surgical operations or application of cast/splint. However, when a nonsurgical treatment is used, cast/splint has to be applied to immobilize adjacent joints. Since it usually takes about two months for fractured bones to heal, the cast/splint immobilization often causes muscle weakness or joint stiffness, which requires rehabilitation to restore normal activity of the patient. On the other hand, for surgical operations, skin incision must be made at the fracture site. Usually, a large wound about 10-12 cm has to be made. Wound complications such as pain or infection may occur after the surgical operation, and cause increased morbidity of the patient.

FIGS. 1A and 1B show a conventional way of holding a broken bone. The conventional way of surgical operation, when applied, for example, to treat patella fracture, is first making an incision 100 through which a Kirschner pin 110 is inserted and then twisting a steel wire 120 in a figure of eight. However, the conventional tension band wiring technique has the drawbacks of (1) making a large wound by the incision, which require a long period of time to heal and (2) the large wound often causing extensive soft tissue dissection and periosteal stripping and damaging vascular supply of fracture site, which in turn affects the healing of fractured bone. Further, the large wound is susceptible to easy infection and unnecessary pain, and extension of healing time.

FIGS. 1C and 1D show another conventional way for holding a broken bone, which is applied to treating fracture of distal fibula (lateral malleolar) or olecranon. An incision 100 is first made on the fracture site. A driller 130 is used to do drilling on the bone in order to make a fixation hole 140 in the bone. A steel wire 120 is put through the fixation hole 140. Kirschner pins 110 are inserted into the patient's body at the fracture site through the incision 100 and are fixed by being twisted around by the steel wire 120. This way of holding a broken bone shares the same drawbacks as the previously discussed manner for treating patella fracture.

Thus, the present invention aims to provide a minimally invasive skeletal fixation device, which requires only size reduced incisions and realize improvement of performance of surgical operation to thereby facilitate recovery of the patient and reduction of pain.

SUMMARY OF THE INVENTION

An objective of the present invention is to provide a minimally invasive skeletal fixation device, which is composed of two arcuate tubes and two positioning members, for providing the advantages of small incision size, simple structure, improvement of performance of surgical operation, and flexible adjustment of installation sites of Kirschner pins (K-pins) according to the fracture of bone so as to enhance practicability, innovation, and improvement of the present invention.

Another objective of the present invention is to provide a minimally invasive skeletal fixation device, which is composed of two arcuate tubes and two positioning members, the device further includes a bar member to provide the advantages of enhancing convenience of operation and precision of hole drilling and also improving performance of surgical operations so as to enhance practicability and improvement of the present invention.

To realize the above objectives, the present invention provides a minimally invasive skeletal fixation device comprising two arcuate tubes and two positioning members, wherein each arcuate tube comprises a handle section and a connection section extending from the handle section. Each arcuate tube comprises a hollow tubular portion extending from a first end of the connection section to a second end of the connection section. The hollow tubular portion is formed within inner of each connection section, and a first opening forming at the first end of each connection section and a second opening forming at the second end of each connection section are provided such that the first openings of the two connection sections are set to oppose and to be coupled to each other to have the two hollow tubular portions communicating with each other. The positioning members are coupled to the handle sections of the arcuate tubes. As such, the advantages of small incision size, simple structure, easy operation, improved performance of surgical operations, and flexible adjustment of installation sites of K-pins according to the fracture of bone can be realized, which help enhancing practicability, innovation, improvement, and convenience of the present invention. Further, the two arcuate tubes can alternatively coupled with a bar member in order to improve the convenience and precision of hole drilling, which helps reducing the influence of frequent use of X-ray machines on the human health of patients and operators so as to enhance practicability, improvement, and convenience of the present invention.

BRIEF DESCRIPTION OF THE DRAWINGS

The present invention will be apparent to those skilled in the art by reading the following description of preferred embodiments thereof with reference to the drawings, in which:

FIGS. 5D-5J show an application of the minimally invasive skeletal fixation device according to the fourth embodiment of the present invention; in which FIG. 5I is side view of FIG. 5H.

DETAILED DESCRIPTION OF THE PREFERRED EMBODIMENTS

First Embodiment

Figure 1A:
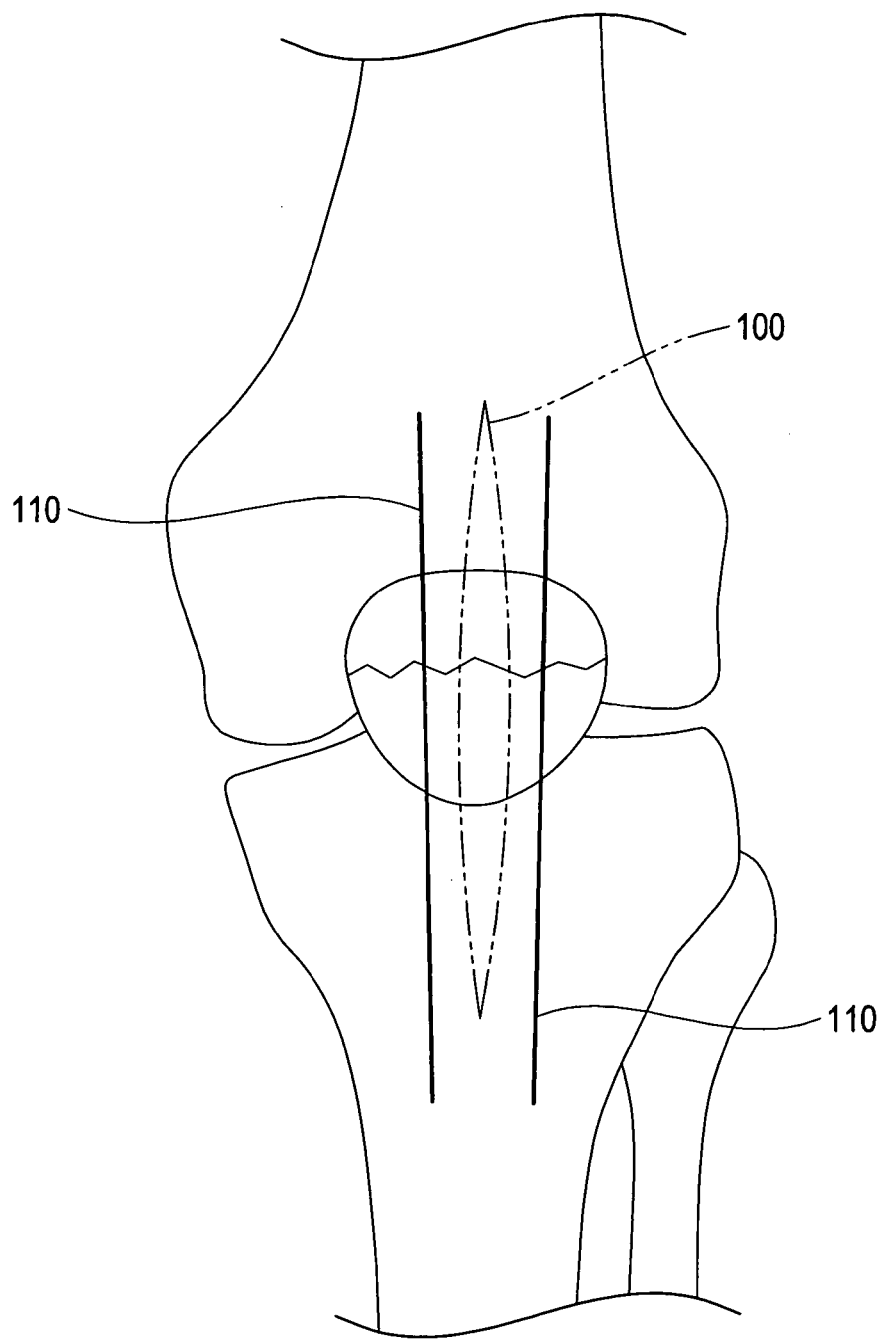
FIGS. 1A-1D show conventional ways of holding a broken bone.
Figure 1B:
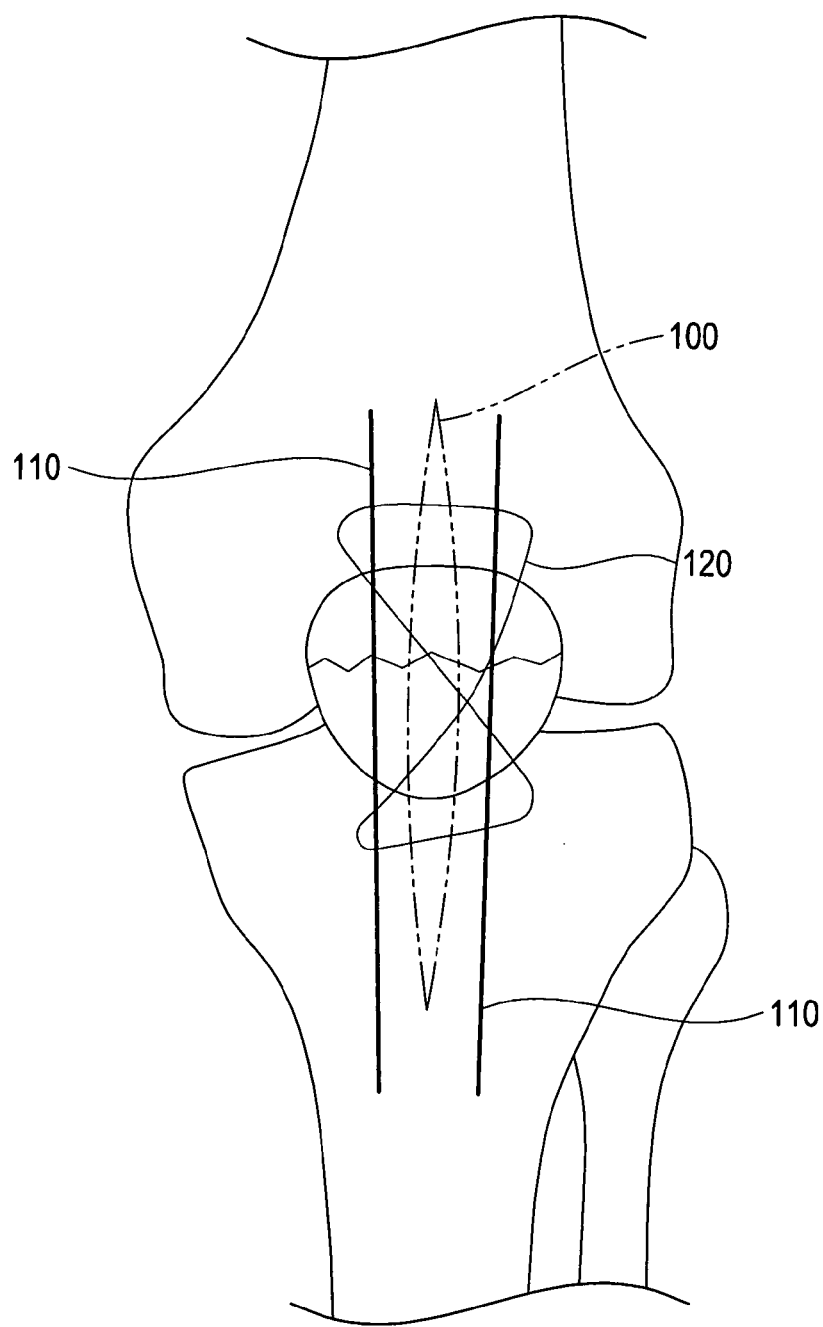
Figure 1C:
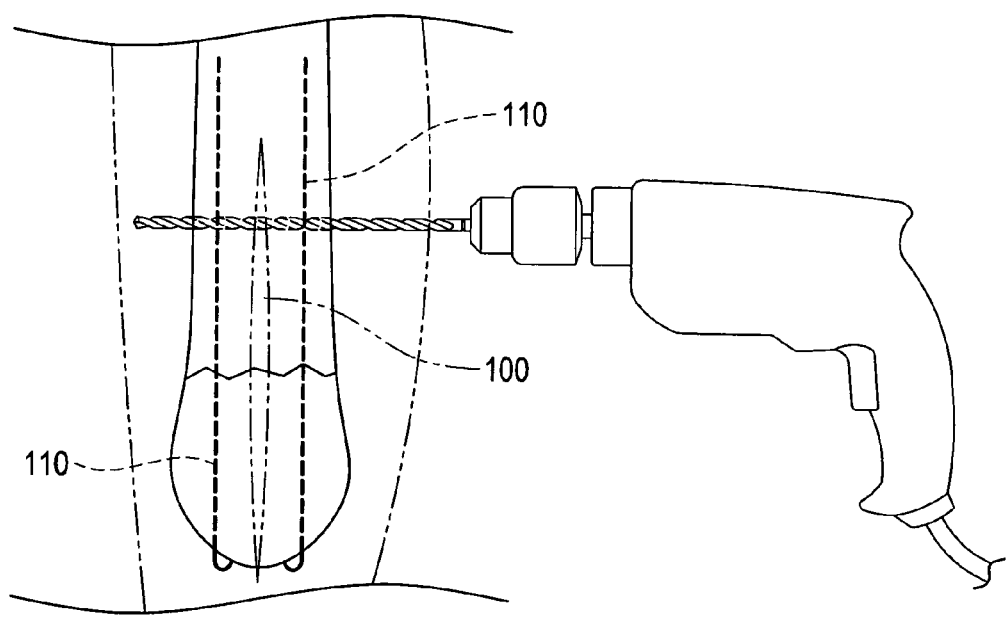
Figure 1D:
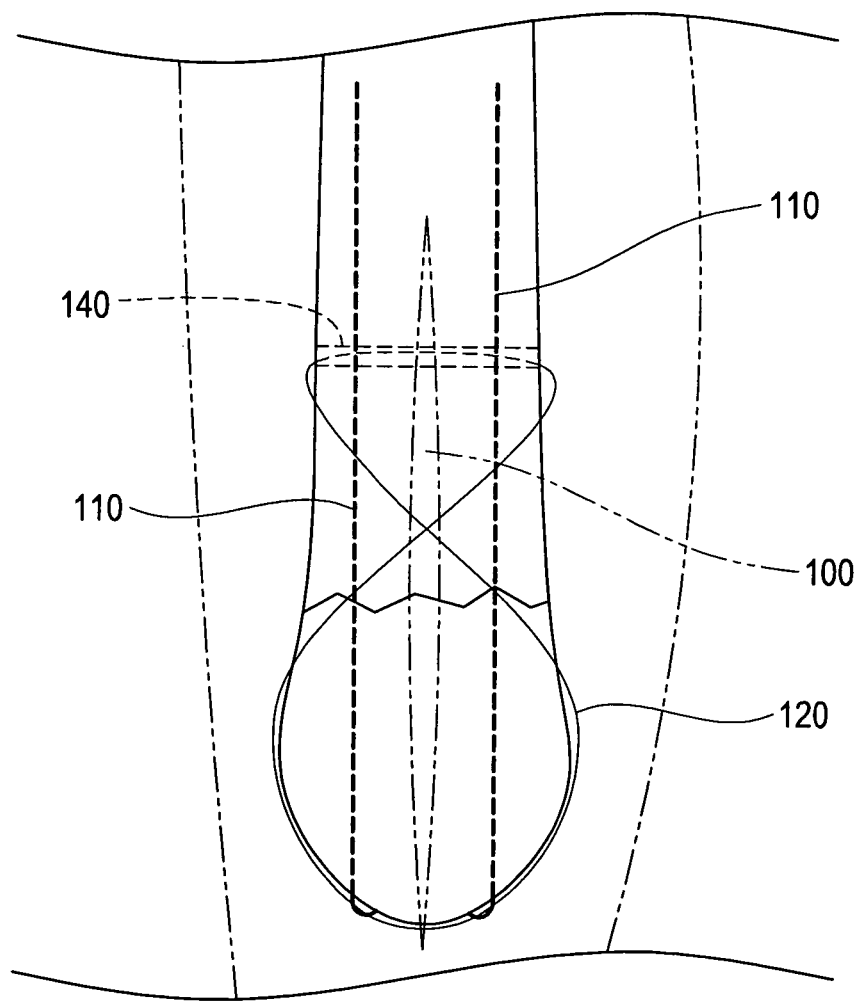
Figure 2A:
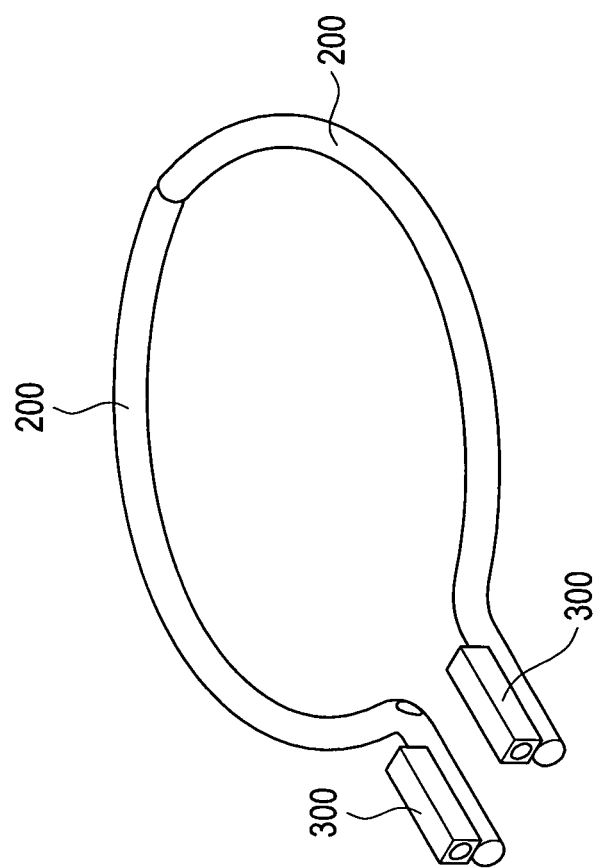
FIG. 2A is a perspective view showing a minimally invasive skeletal fixation device constructed in accordance with a first embodiment of the present invention.
Figure 2B:
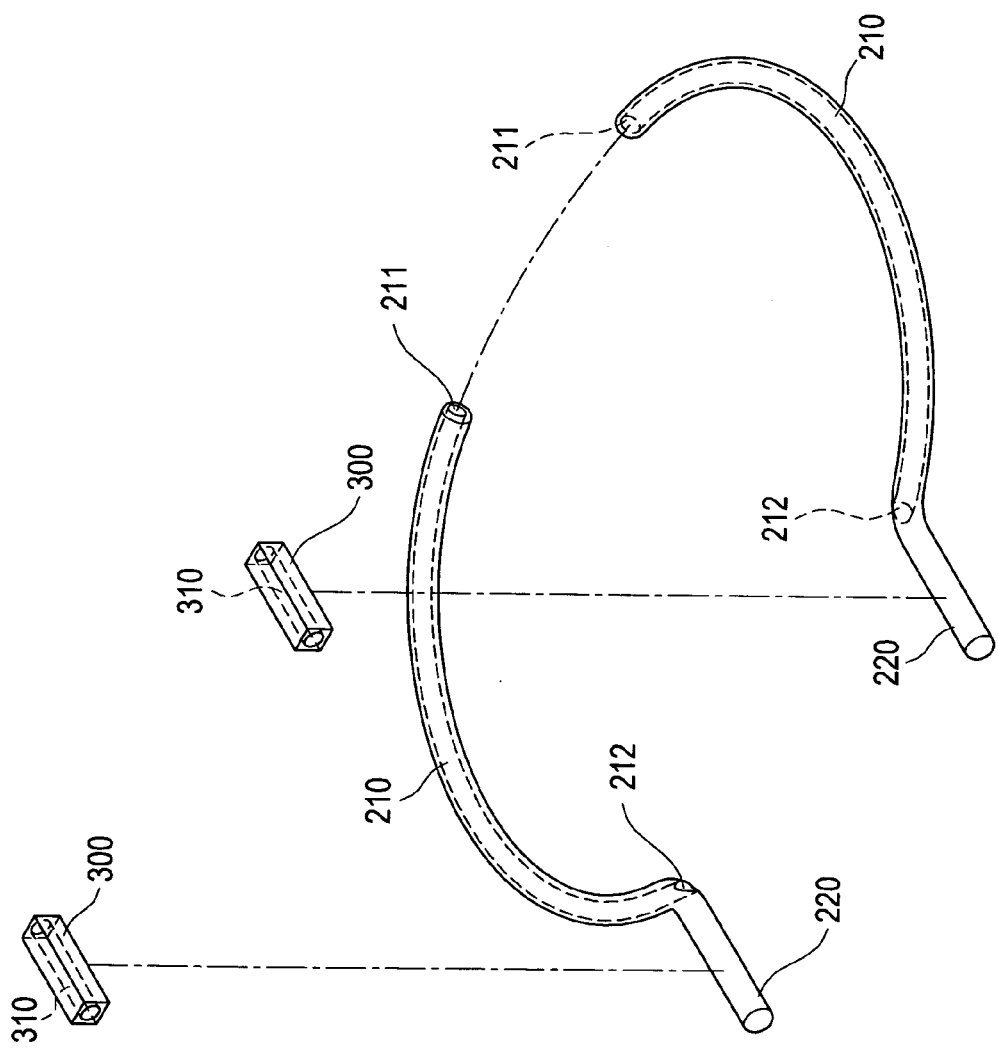
FIG. 2B is an exploded view showing the minimally invasive skeletal fixation device constructed in accordance with the first embodiment of the present invention.
Figure 2C:
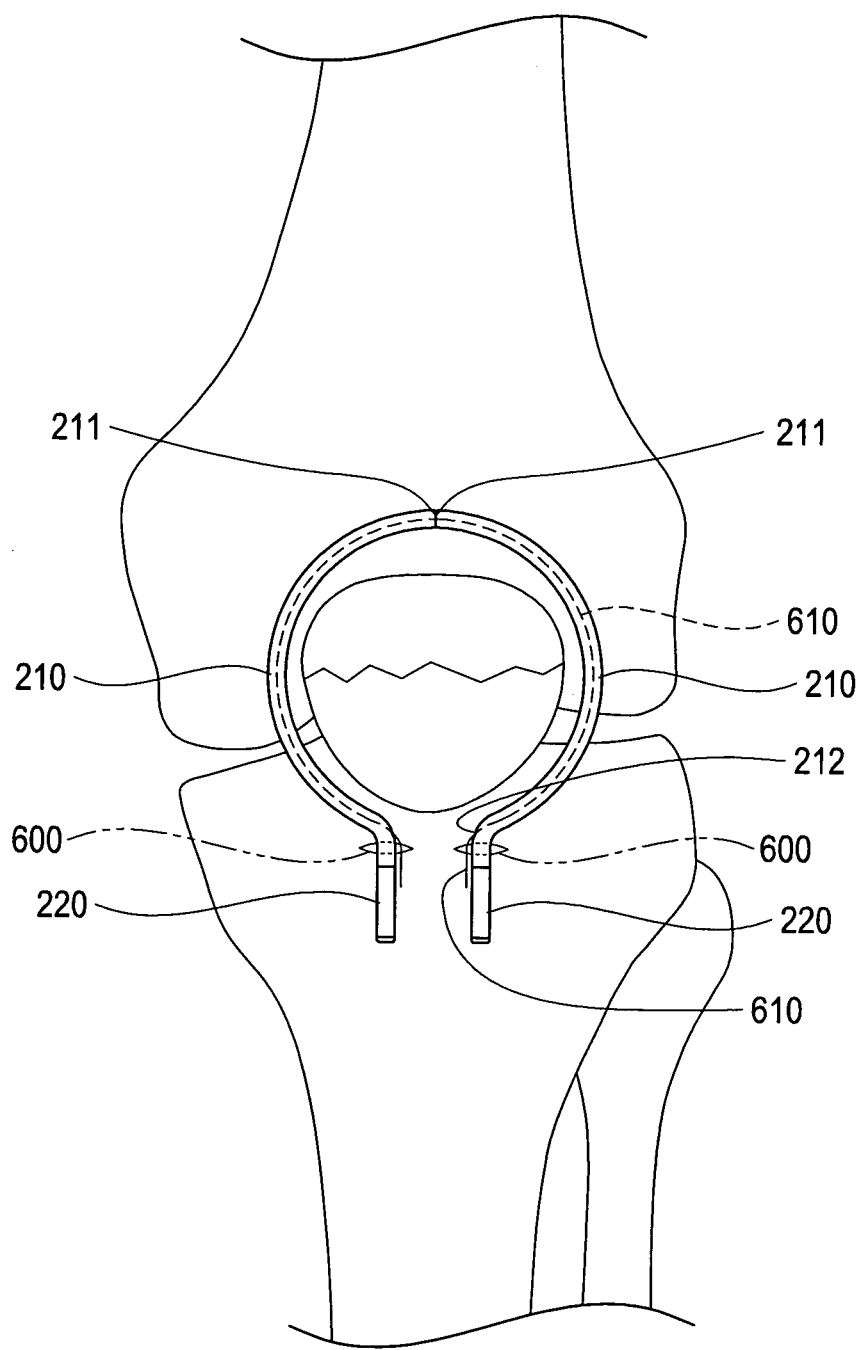
FIGS. 2C-2E show an application of the minimally invasive skeletal fixation device according to the first embodiment of the present invention.
Figure 2D:
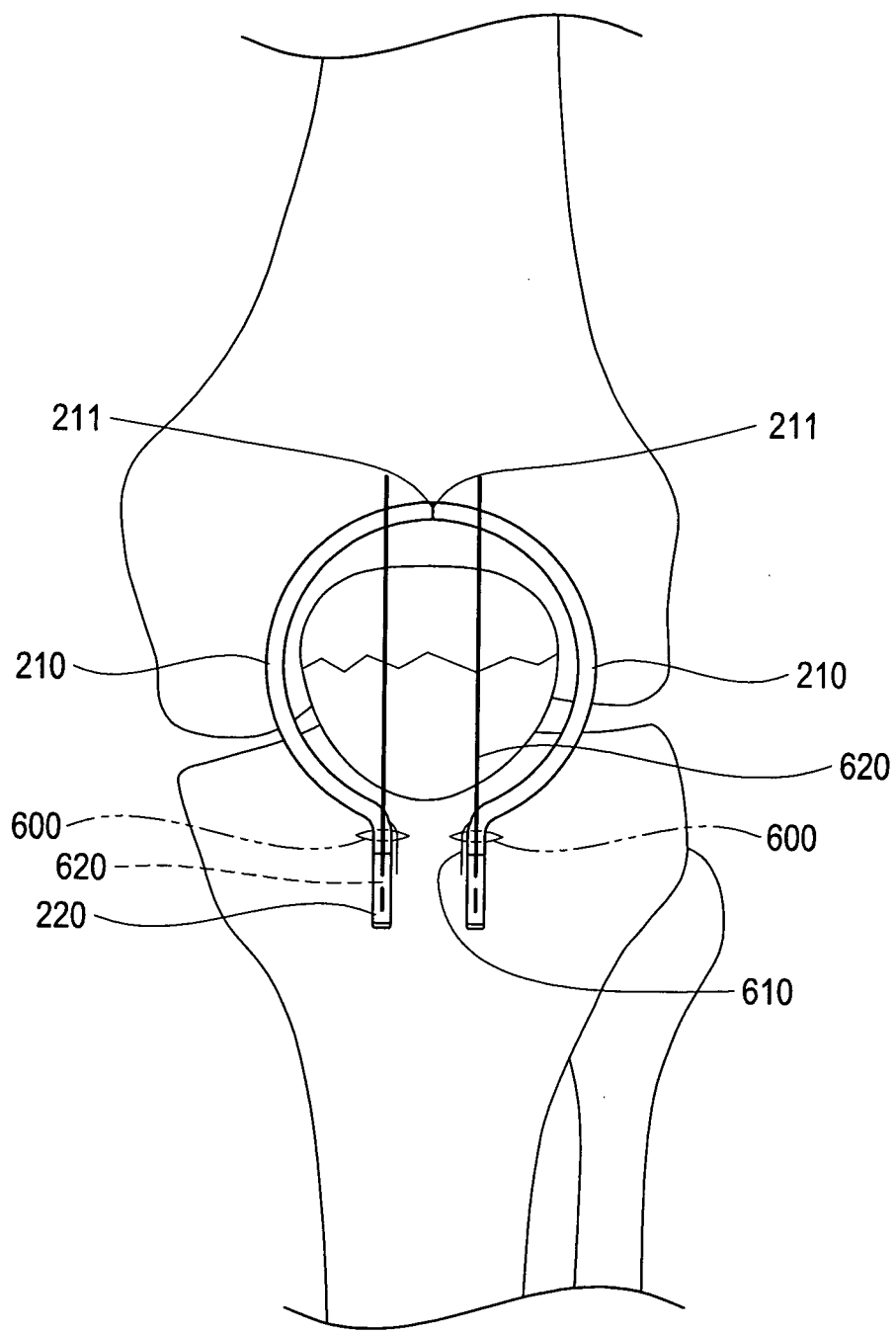
Figure 2E:
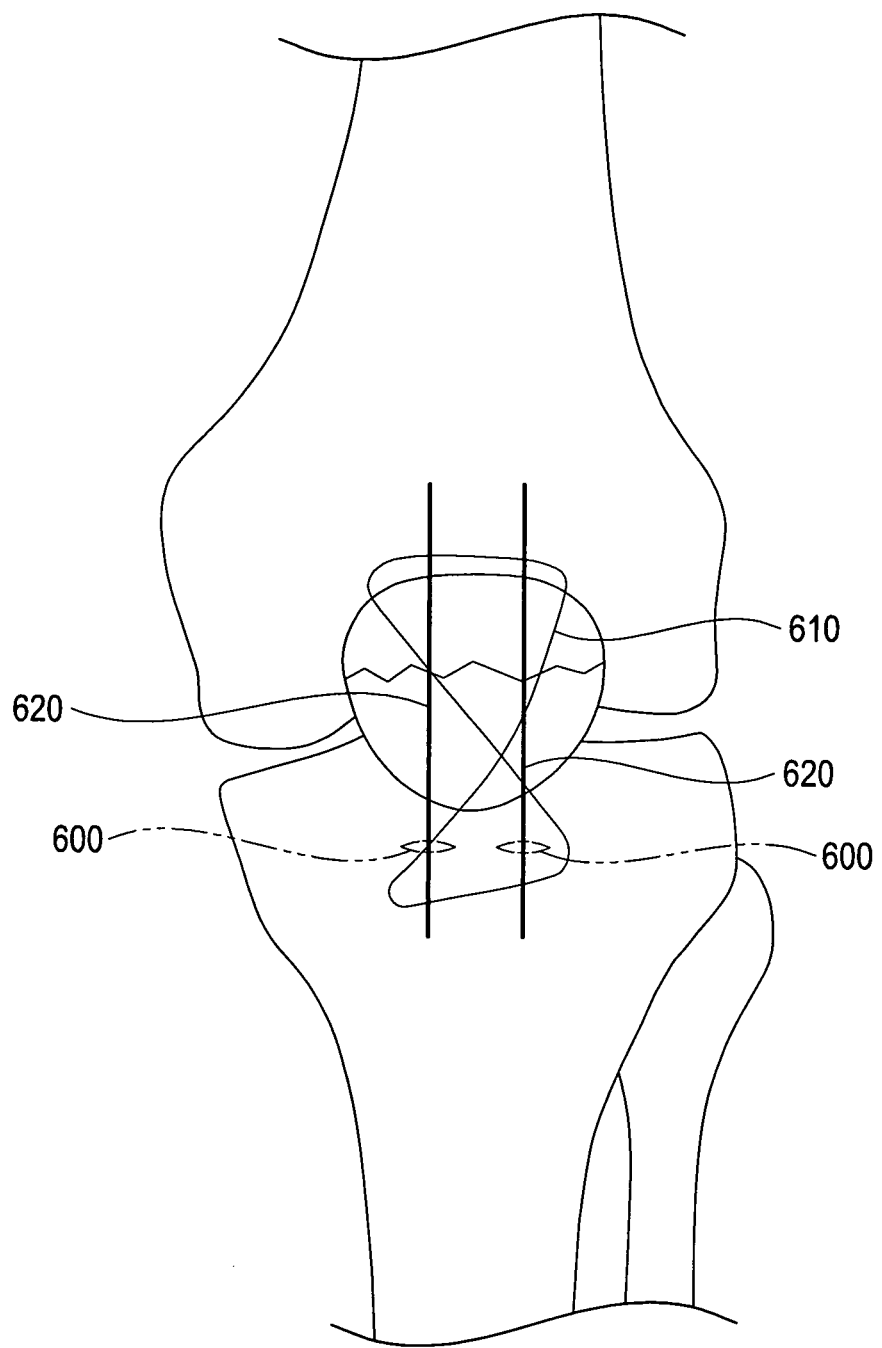

Referring to FIGS. 2A and 2B, which are respectively a perspective view and an exploded view of a minimally invasive skeletal fixation device constructed in accordance with a first embodiment of the present invention, the minimally invasive skeletal fixation device comprises two arcuate tubes 200 and two positioning members 300 with which an incision made in a surgical operation for treating patella fracture of a patient can be made extremely small for fast recovery so as to allow the patient to return normal movement in a short period.

Each arcuate tube 200 is in the form of a hook like arcuate tube (which includes an arcuate section and a straight section). Each arcuate tube 200 has a curvature not limited to any specific value. Each arcuate tube 200 comprises a connection section (namely the arcuate section) 210 and a handle section (namely the straight section) 220. Each connection section 210 comprises a hollow tubular portion. The hollow tubular portion extending from a first end of the connection section 210 to a second end of the connection section 210 is formed within inner of each connection section 210, and a first opening 211 forming at the first end of each connection section 210 and a second opening 212 forming at the second end of each connection section 210 are provided such that the first openings 211 of the two connection sections 210 are set to oppose and to be coupled to each other to have the two hollow tubular portions communicating with each other. The connection sections 210 of the arcuate tubes 200 can be of the same diameter or alternatively they can be of different diameters (such that the connection section 210 of one arcuate tube 200 has a diameter greater than that of the connection section 210 of the other arcuate tube 200.) The connection section 210 of each arcuate tube 200 comprises a magnetic body (such as a magnet or magnetic powders) by which the first openings 211 of the connection sections attract and are thus attached to each other. Further, the connection section 210 and the handle section 220 of each arcuate tube 200 can be made in the form inter-communicating tubular portions, meaning the arcuate tube 200 is integrally formed so that the handle section 220 thereof forms an opening (not shown).

Each positioning member 300 comprises a positioning tubular portion with a bore 310 therein (wherein the positioning member 300 has a shape not limited to any specific form). The positioning member 300 is positioned on the handle section 220 of each arcuate tube 200, whereby the arcuate tube 200 and the positioning member 300 are set on different horizontal planes. Each positioning member 300 is coupled to the handle section 220 of each arcuate tube 200 (wherein the coupling can be fixed or removable).

As shown in FIGS. 2A-2E, the application of the minimally invasive skeletal fixation device according to the present invention in a surgical operation of patella fracture starts with making two incisions 600, followed by respectively penetrating the two arcuate tubes 200 through the two incisions 600 to locations around the fractured patella with the first openings 211 of the connection sections 210 of the two arcuate tubes 200 mating and combining with each other. The two hollow tubular portions of each connection sections 210 are made in communication with each other after mating and combining.

Preferably, the connection section 210 of each of the arcuate tubes 200 is provided with a magnetic body (such as a magnet or magnetic powders) to allow the connection sections 210 of the connection sections 210 to attach to each other due to magnetic attraction and thus preventing the connection sections 210 of the arcuate tubes 200 from undesired separation that affects the performance of the surgical operation. Afterwards, a wire member 610 (such as a steel wire) is inserted through the second opening 212 of one of the arcuate tubes 200 (such as the right-hand side arcuate tube 200) and extends out of the second opening 212 of the other one of the arcuate tubes 200 (such as the left-hand side arcuate tube 200), whereby the wire member 610 is received through both arcuate tubes 200. Two Kirschner pins (K-pins) 620 are respectively put through the bores 310 of the positioning members 300 to be located on the patella. Afterwards, the two arcuate tubes 200 are separated and respectively removed out of the two incisions 600 and the wire member 610 is twisted around the K-pins 620 to complete fixation. Finally, the incisions 600 are stitched to thereby complete the surgical operation. As compared to the known processes of surgical operation, the present invention offers the advantages of significant reduction of incision size, which facilitates shortening recovery period and reduces the potential risk of wound infection so as to allow patients of patella fracture to return normal movement in a short period. Apparently, the present invention improves the performance of surgical operation and realizes convenience of use.

Second Embodiment

Figure 3:
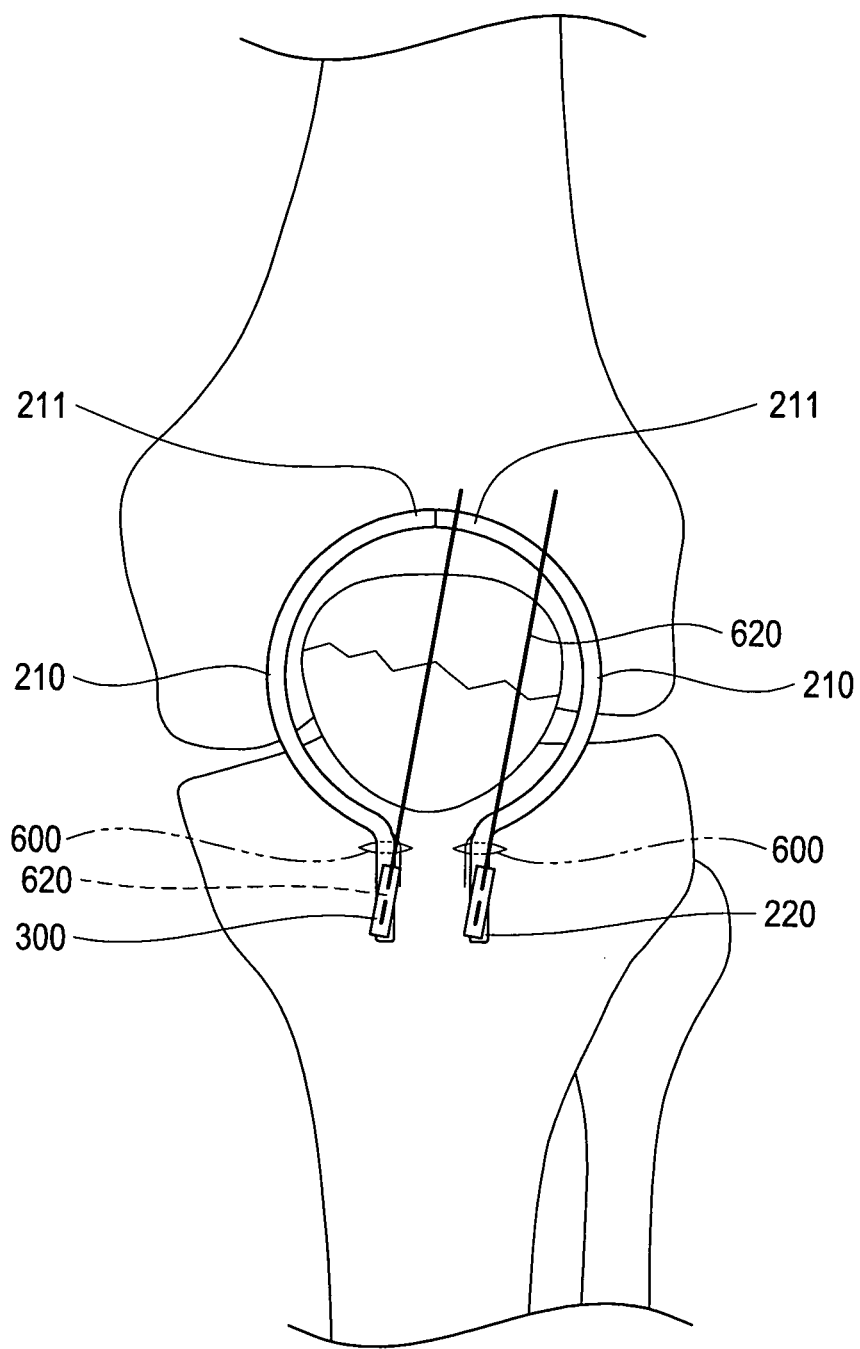
FIG. 3 shows an application of a minimally invasive skeletal fixation device in accordance with a second embodiment of the present invention.

Referring to FIG. 3, which shows an application of a minimally invasive skeletal fixation device in accordance with a second embodiment of the present invention, the minimally invasive skeletal fixation device of the second embodiment is substantially identical to that of the first embodiment and a difference between the two embodiments resides in that in the second embodiment, the positioning members 300 are respectively coupled to the handle sections 220 of the arcuate tubes 200 in a removable manner (for example, the positioning members 300 being coupled to the handle sections 220 of the arcuate tubes 200 with a pivotal joint or a threaded connection), whereby the positioning members 300 allow for adjustment of angles thereof.

Thus, the minimally invasive skeletal fixation device according to the second embodiment of the present invention allows for flexible adjustment of the installation sites of the K-pins 620. As compared to the known processes of surgical operation, the present invention offers enhanced convenience of use in surgical operations.

Third Embodiment

Figure 4:
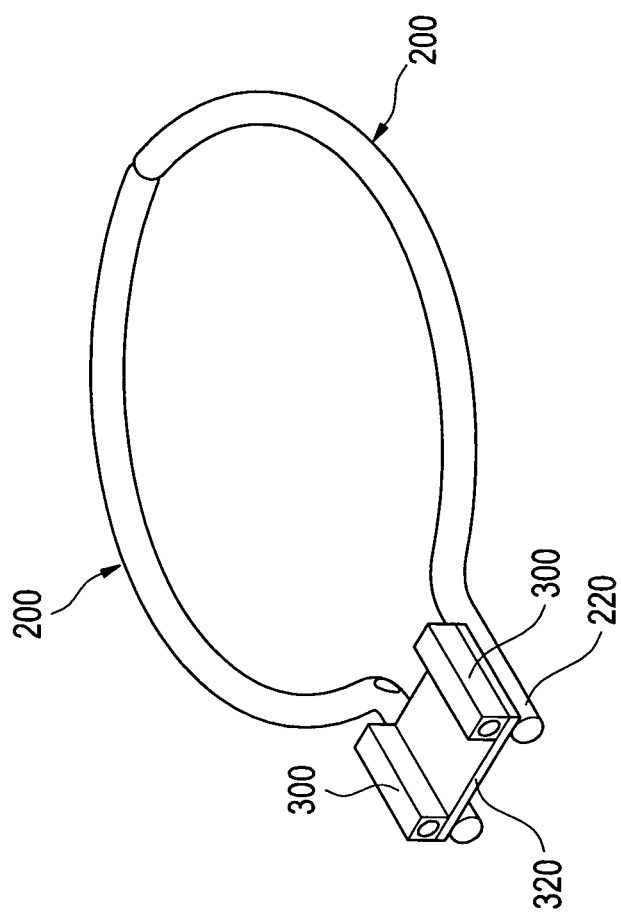
FIG. 4 shows a perspective view of a minimally invasive skeletal fixation device constructed in accordance with a third embodiment of the present invention.

Referring to FIG. 4, which shows a perspective view of a minimally invasive skeletal fixation device in accordance with a third embodiment of the present invention, the minimally invasive skeletal fixation device of the third embodiment is substantially identical to that of the first embodiment and a difference between the two embodiments resides in that in the third embodiment, a pad 320 (which comprises a board in the embodiment illustrated, but can be of any other desired shape) is provided between each curved tube 200 and each positioning member 300. With the arrangement of the pad 320 between each arcuate tube 200 and each positioning member 300, the curved tube 200 and the associated positioning member 300 are more surely set at different horizontal planes to facilitate extension of twisting of the wire member 610 around the K-pins 620 for fixation. Particularly, the pad 320 is provided between two arcuate tubes 200. With the arrangement of the pad 320 between two arcuate tubes 200, the two arcuate tubes 200 are surely set at the same horizontal plane to make two openings 211 oppose and attach to each other, so that the two hollow tubular portions of the two connection section 210 surly communicate with each other.

Fourth Embodiment

Figure 5A:
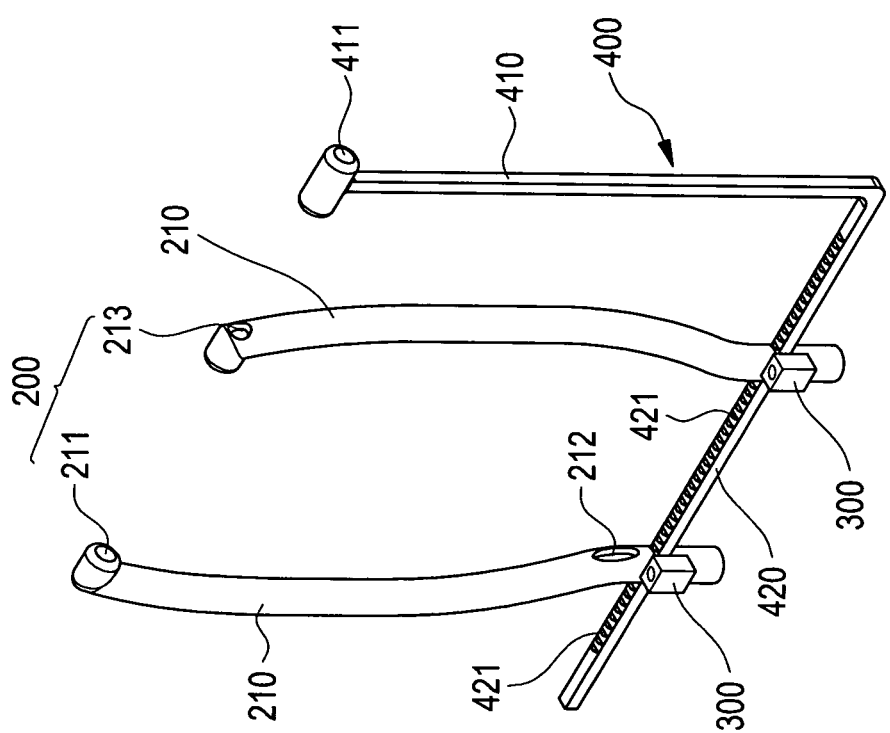
FIG. 5A is a perspective view showing a minimally invasive skeletal fixation device constructed in accordance with a fourth embodiment of the present invention.
Figure 5B:
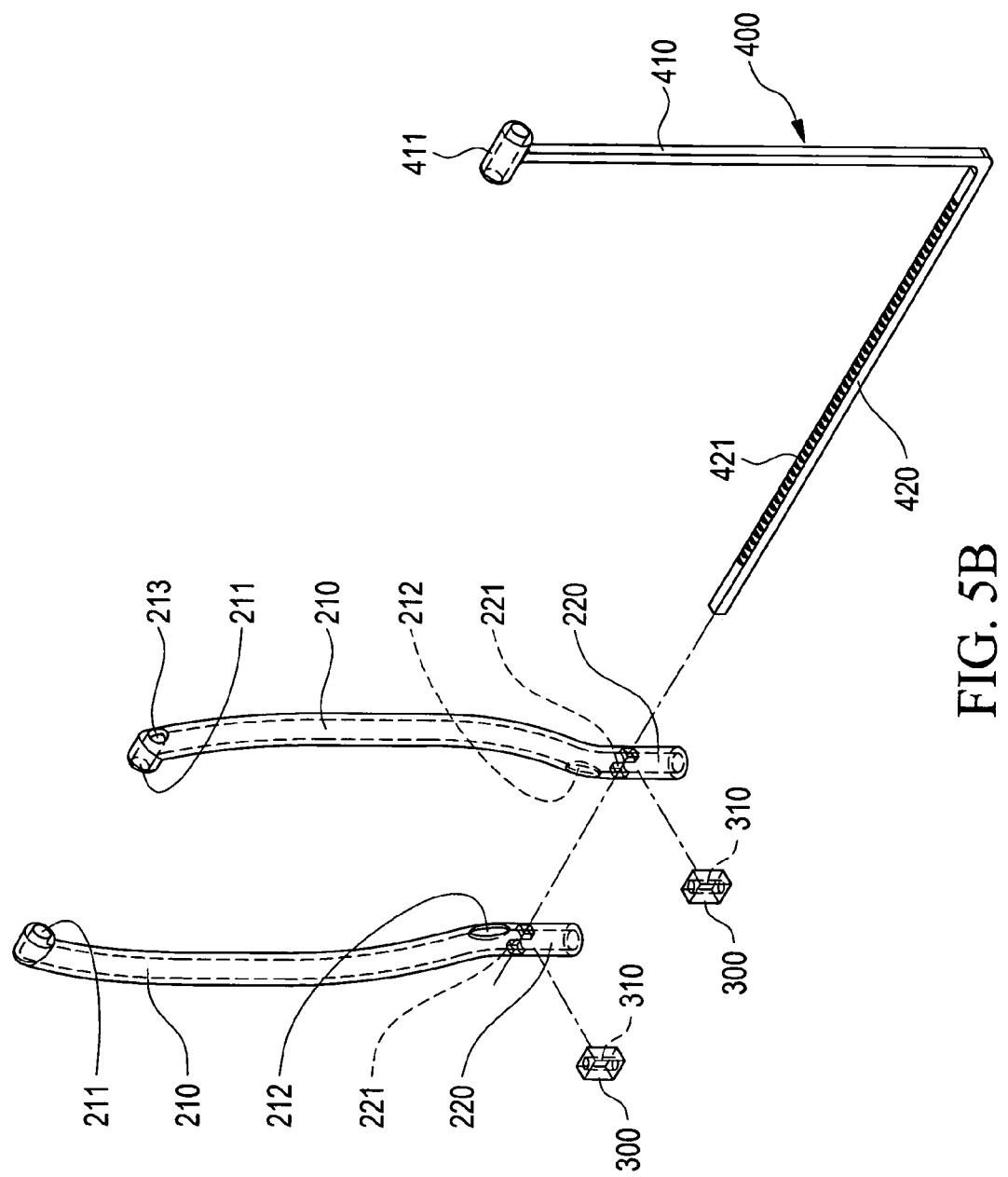
FIGS. 5B and 5C are exploded views of the minimally invasive skeletal fixation device in accordance with the fourth embodiment of the present invention.
Figure 5C:
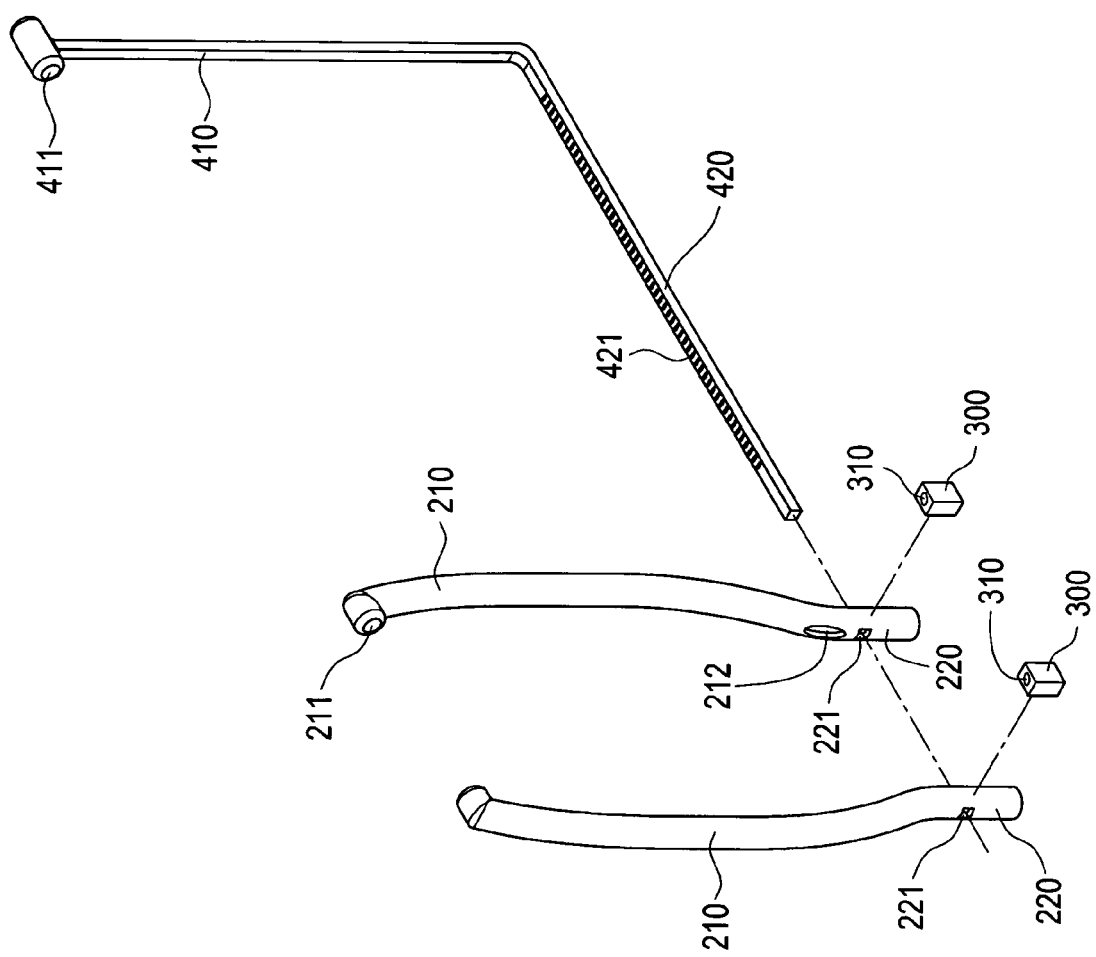
Figure 5D:
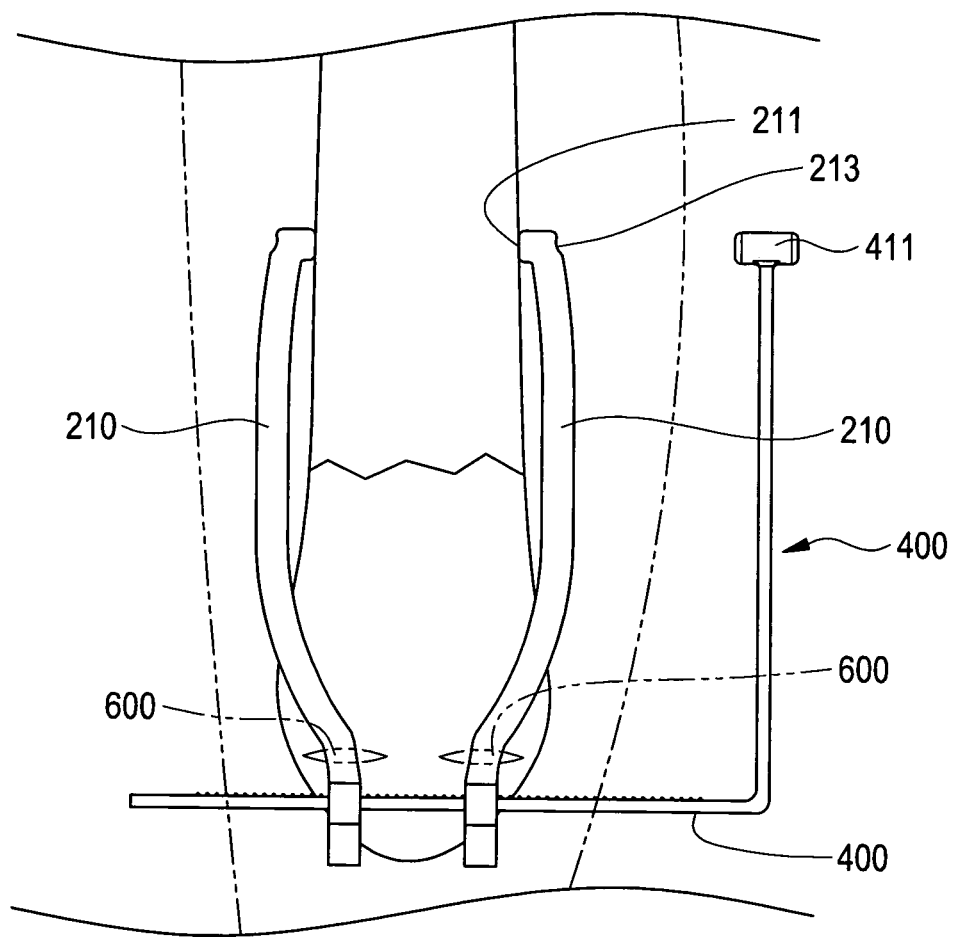
Figure 5E:
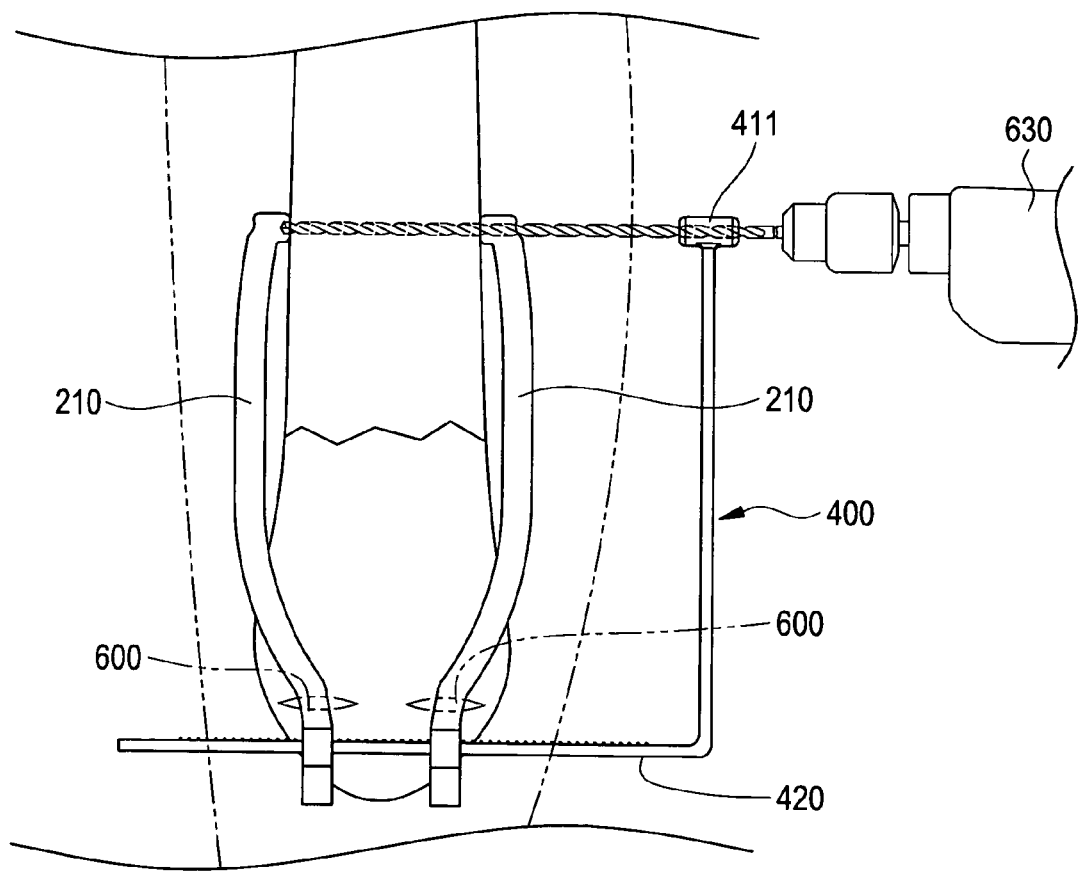
Figure 5F:
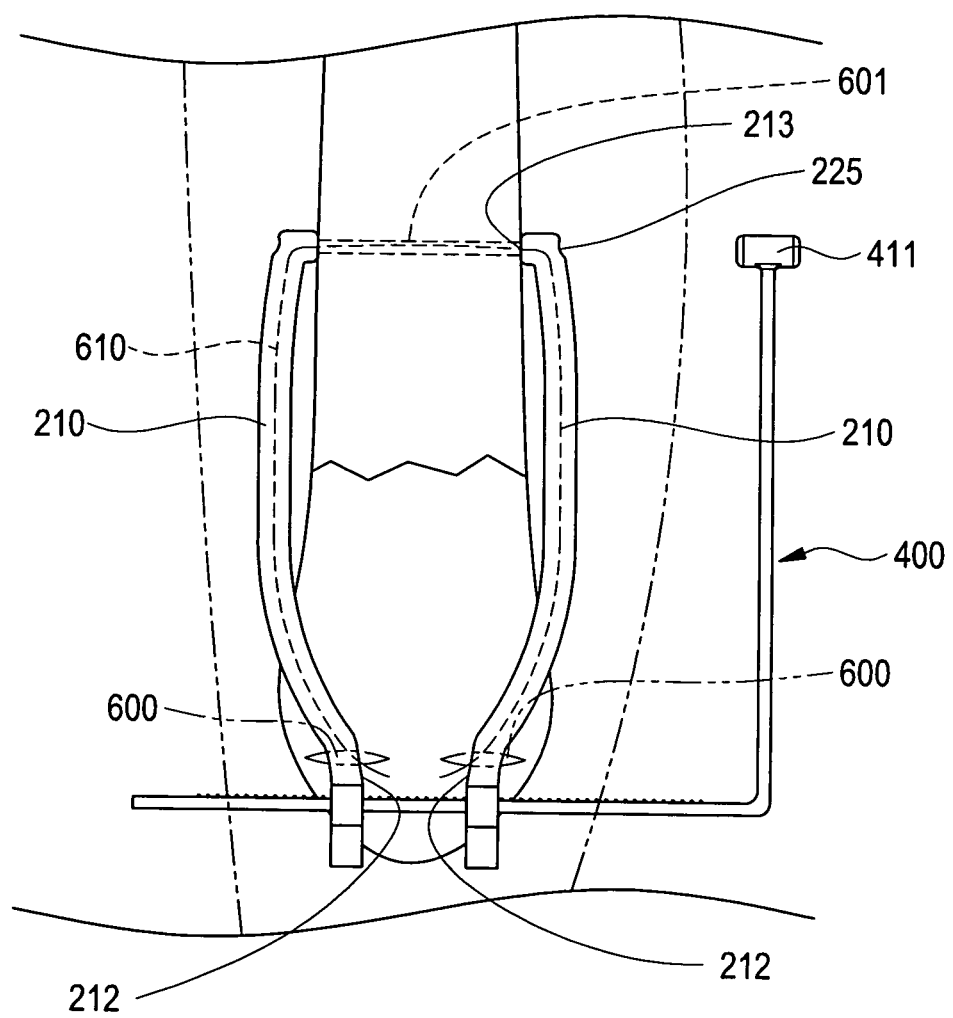
Figure 5G:
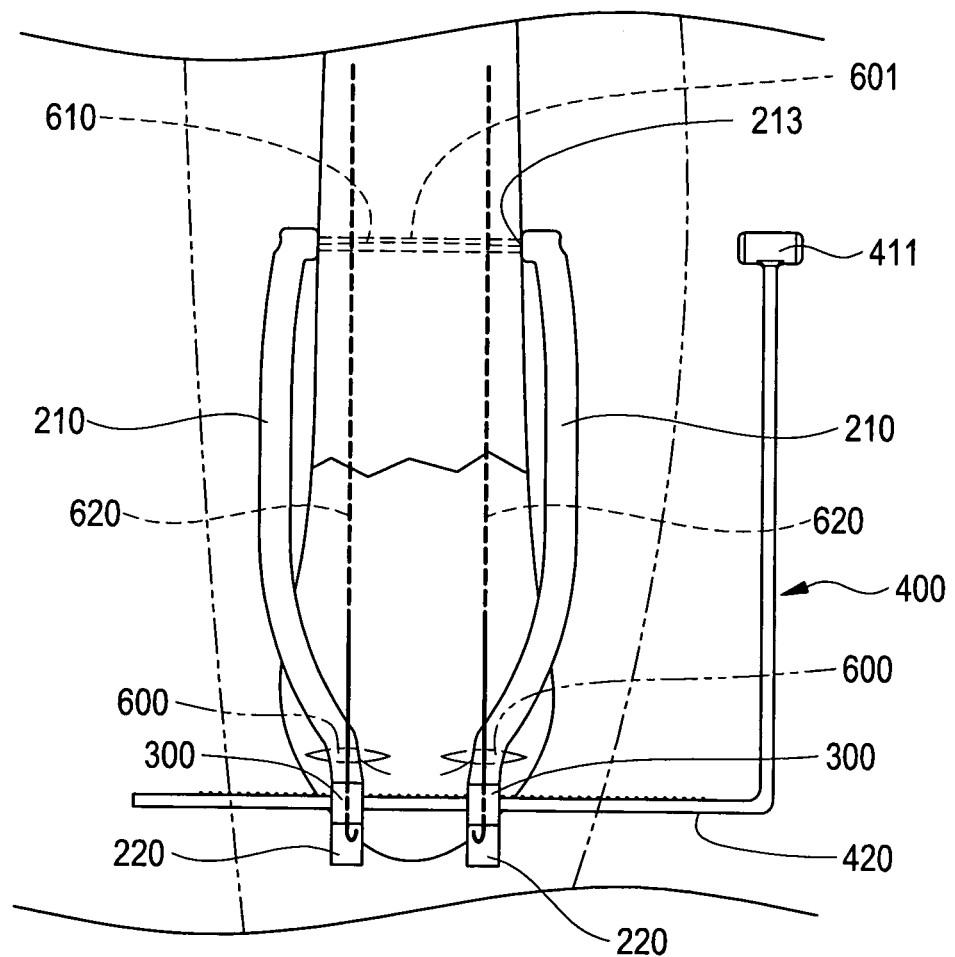
Figure 5H:
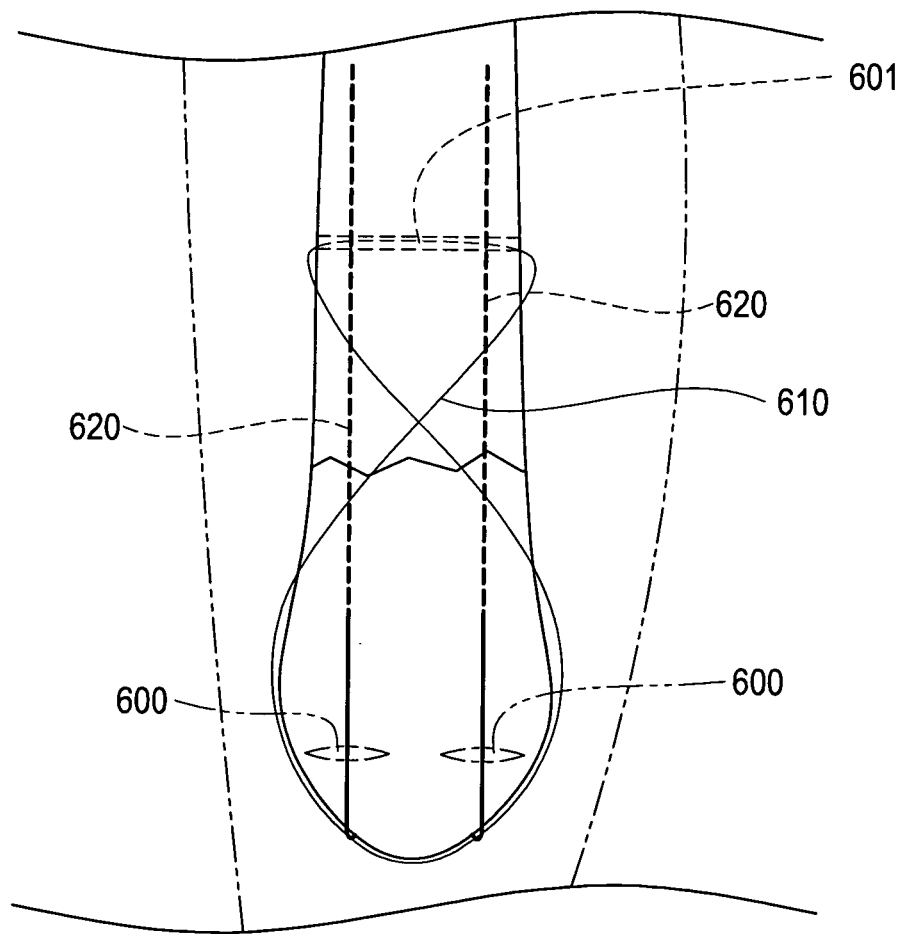
Figure 5I:
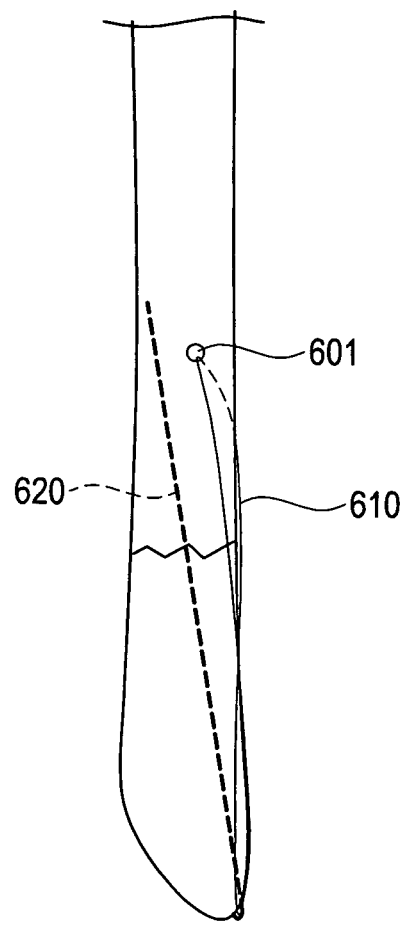
Figure 5J:
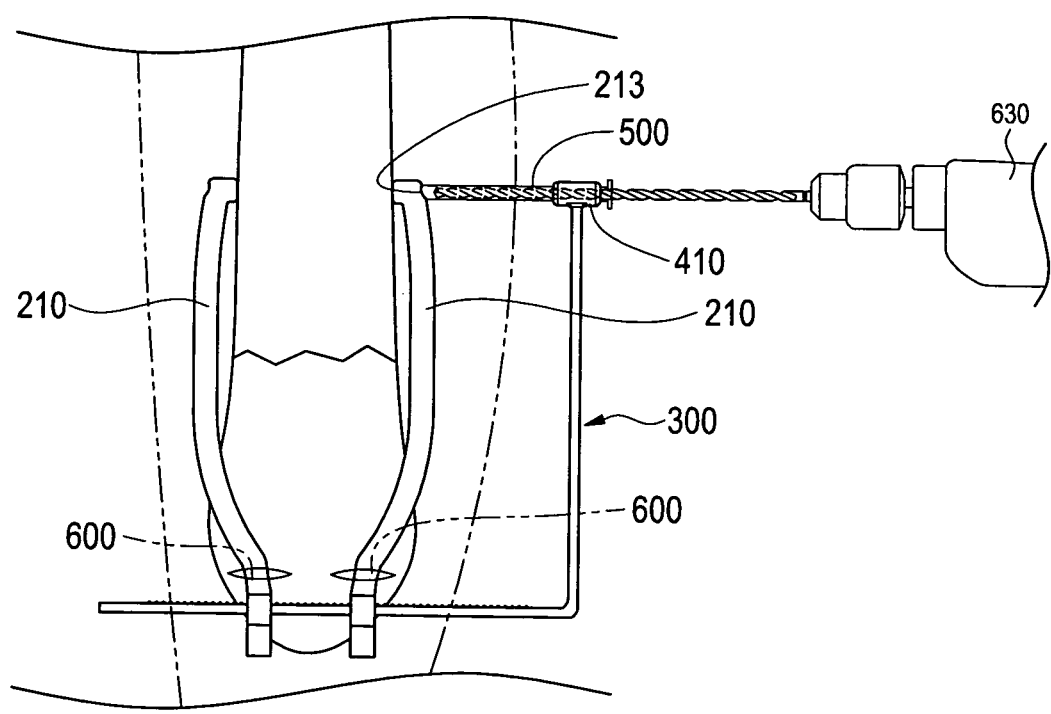

Referring to FIGS. 5A-5C, which are respectively a perspective view and two exploded views showing a minimally invasive skeletal fixation device in accordance with a fourth embodiment of the present invention, the minimally invasive skeletal fixation device of the fourth embodiment is substantially identical to that of the first embodiment and a difference between the two embodiments resides in that besides the two arcuate tubes 200 and the two positioning members 300, the minimally invasive skeletal fixation device of the fourth embodiment further comprises a bar member 400 for realizing precise hole drilling in a surgical operation for treating leg fracture in order to improving performance of the surgical operation.

In the fourth embodiment, each arcuate tube 200 comprises a connection section 210 and a handle section 220. The arcuate tube 200 comprises a first opening 211 and a second opening 212. Each handle section 220 forms a fixation hole 221, which is a through hole, and the fixation holes 221 of the two handle sections 220 oppose to each other. The connection section 210 of one of the arcuate tubes 200 forms a first through hole 213, which is in communication with the first opening 211 of the connection section 210.

The bar member 400 (which is an L-shaped bar in the embodiment illustrated) comprises a facing section 410 and an adjustment section 420 connected to the facing section 410. The facing section 410 forms a second through hole 411; which opposes the first through hole 213 of the arcuate tube 200, whereby the first openings 211, the first through holes 213, and the second through hole 1 are put in alignment with each other along a straight line for precise positioning for hole drilling. The adjustment section 420 of the bar member 400 are fit through the fixation holes 1 of the arcuate tubes 200 and the adjustment section 420 comprises a plurality of adjustment pieces 421 (such as resilient elements or projections) that are engageable with the fixation hole 221 of each arcuate tube 200 for position adjustment to improve the performance of a surgical operation.

As shown in FIGS. 5A-5J, the drilling-assisting minimally invasive skeletal fixation device in accordance with this embodiment is applicable to a surgical operation for treating fracture of distal fibula or olecranon, which starts with making two incisions 600 through which the two arcuate tubes 200 are penetrated to the location of fracture and located on opposite sides of the fracture bone. The adjustment section 420 of the bar member 400 is fit through the fixation hole 221 of each of the arcuate tubes 200. Afterwards, a drill bit of a driller 630 is put in alignment with the first openings 211 and the first through holes 213 of the arcuate tubes 200 to carry out drilling, whereby the drill bit of the driller 630 is allowed to carry out drilling from one of the arcuate tubes 200 to reach the first opening 211 of the other arcuate tube 200 to form a fixation hole 601 in the leg bone. Correction of the relative position of the fixation hole 601, which often affects the performance of the surgical operation and also causes concerns of health for the patient and the operators, can be eliminated.

Afterwards, since the connection sections 210 of the arcuate tubes 200 has hollow tubular portions, the connection sections 210 and the fixation hole 601 can be made in communication with each other, whereby a wire member 610 (such as a steel wire) is inserted through the second opening 212 of one of the arcuate tubes 200, goes through the fixation hole 601, and then extends out of the second opening 212 of the other one of the arcuate tubes 200 and the wire member 610 is thus received through the connection sections 210 of the two arcuate tubes 200 and the fixation hole 601. Two K-pins 620 are respectively put through the positioning members 300 to be located intramedullary or have distal ends projecting through bone cortex. Afterwards, the two arcuate tubes 200 are removed out of the incisions 600 and the wire member 610 is twisted around the K-pins 620 to complete fixation. Finally, the incisions 600 are stitched to thereby complete the surgical operation. As compared to the known processes of surgical operation, the embodiment of the present invention offers the advantages of improvement of precise extension of the wire member 610 after drilling and reduction of the influence of repeated operations of an X-ray machine on human health of the patient and the operators and also helps in significant reduction of incision size, which facilitates shortening recovery period and reduces the potential risk of wound infection so as to allow patients of patella fracture to return normal movement in a short period. The present invention improves the performance of surgical operation and realizes convenience of use. Further, a sleeve 500 (see FIG. 5I) can be additionally provided between the first through hole 213 of one of the arcuate tubes 200 and the second through hole 411 of the bar member 400 in such a way that the sleeve 500 is in communication with both the first through hole 213 and the second through hole 411, whereby in the performance of a drilling operation by a drill bit of a driller 630, the drill bit of the driller 630 can be received through the sleeve 500 in order not to hurt soft tissues during the drilling operation. Further, the wire member 610 can be inserted along a path extending through the sleeve 500.

The minimally invasive skeletal fixation device of the present invention has the features that through the use of two arcuate tubes 200 and two positioning members 300, advantages of small incision size, simple structure, easy operation, improvement of performance of surgical operation, and flexible adjustment of installation sites of K-pins according to the fracture of bone are realized, which help enhancing practicability, innovation, and improvement of the present invention; and through the arrangement of the arcuate tubes 200 coupled with a bar member 400, the convenience and precision of hole drilling is improved, which helps reducing the influence of frequent use of X-ray machines on the human health of patients and operators and improving the performance of surgical operation to thereby enhance practicability, innovation, and improvement of the present invention.

Although the present invention has been described with reference to the preferred embodiments thereof, it is apparent to those skilled in the art that a variety of modifications and changes may be made without departing from the scope of the present invention which is intended to be defined by the appended claims.

The invention claimed is:

1. A minimally invasive skeletal fixation device, comprising:
two arcuate tubes, each of which comprises a handle section and a connection section extending from the handle section, wherein the inner of the connection section being formed with a hollow tubular portion, ends of the hollow tubular portion being with a first opening and a second opening, the first openings of the two connection sections are set to oppose and to be coupled to each other to have the two hollow tubular portions communicating with each other;

two positioning members, each of which comprising a positioning tubular portion with a bore therein and is respectively coupled to each handle section, whereby the arcuate tube and the positioning member are set on different horizontal planes, and the positioning members are coupled to the handle sections of the arcuate tubes in a fixed or removable manner;

a pad arranged between the two arcuate tubes; and a bar member including a facing section and a adjustment section connected to the facing section, the adjustment section being coupled to the handle sections of the arcuate tubes, the handle section of each of the arcuate tubes forming a fixation hole through which the adjustment section of the bar member is received so as to couple the bar member to the arcuate tubes, wherein the connection section of one of the arcuate tubes forms a first through hole, which communicates with the first opening, the facing section of the bar member forming a second through hole opposing the first through hole, and a sleeve is arranged between the first through hole of the arcuate tube and the second through hole of the bar member, the sleeve being in communication with the first and second through holes.

* * * * *

UNITED STATES PATENT AND TRADEMARK OFFICE
CERTIFICATE OF CORRECTION

PATENT NO. : 8,579,900 B2  
APPLICATION NO. : 12/654851  
DATED : November 12, 2013  
INVENTOR(S) : Chia-Hao Hsu It is certified that error appears in the above-identified patent and that said Letters Patent is hereby corrected as shown below:

In the Claims

Claim 1, Column 7, lines 1-4, delete the following text "the inner of the connection section being formed with a hollow tubular portion, ends of the hollow tubular portion being with a first opening and a second opening," and insert the following in its place:

--the interior of the connection section being formed with a hollow tubular portion, said hollow tubular portion having a first opening at a first end and a second opening at a second end,--

Signed and Sealed this  
Eleventh Day of February, 2014

Michelle K. Lee  
*Deputy Director of the United States Patent and Trademark Office*